United States Patent
Tan et al.

(10) Patent No.: US 7,405,828 B2
(45) Date of Patent: Jul. 29, 2008

(54) METHOD FOR MEASURING THE DEGREE OF CROSSLINKING OF PRESSURE SENSITIVE ADHESIVE

(75) Inventors: Yi-Hui Tan, Taoyuan County (TW); Hao-Fei Kuo, Taoyuan County (TW); Jen-Yen Lo, Taipei County (TW)

(73) Assignee: Daxon Technology Inc., Taoyuan (TW)

( * ) Notice: Subject to any disclaimer, the term of this patent is extended or adjusted under 35 U.S.C. 154(b) by 224 days.

(21) Appl. No.: 11/453,805

(22) Filed: Jun. 16, 2006

(65) Prior Publication Data
US 2007/0139650 A1 Jun. 21, 2007

(30) Foreign Application Priority Data
Dec. 15, 2005 (TW) .............................. 94144442 A

(51) Int. Cl.
*G01N 21/00* (2006.01)
*G01N 21/47* (2006.01)

(52) U.S. Cl. .................. 356/446; 356/338; 356/432
(58) Field of Classification Search ................ None
See application file for complete search history.

(56) References Cited
U.S. PATENT DOCUMENTS
6,797,741 B1 * 9/2004 Heino .................. 522/157

* cited by examiner

*Primary Examiner*—Gregory J. Toatley, Jr.
*Assistant Examiner*—Amanda H Merlino
(74) *Attorney, Agent, or Firm*—Birch, Stewart, Kolasch & Birch, LLP

(57) ABSTRACT

A method for measuring the degree of crosslinking of pressure sensitive adhesive. The method, having the advantages of simple steps and short measuring time, comprises immersing a transparent substrate coated with a pressure sensitive adhesive in a solvent. After a specific period, the haze of the transparent substrate is measured. The obtained haze is compared with a predetermined reference, thereby determining the degree of crosslinking of the pressure sensitive adhesive.

10 Claims, 4 Drawing Sheets

METHOD FOR MEASURING THE DEGREE OF CROSSLINKING OF PRESSURE SENSITIVE ADHESIVE

BACKGROUND OF THE INVENTION

1. Field of the Invention

The invention relates to a method for measuring the in pressure sensitive adhesive, and more particularly to a method for measuring the degree of crosslinking in pressure sensitive adhesive, having the advantages of simplification and short measurment time.

2. Description of the Related Art

Pressure-sensitive adhesive refers to an adhesive which bonds to an application surface as a result of applied pressure. In general, the pressure-sensitive adhesive comprising organic polymers exhibits adhesion over a long period of time. Since the pressure-sensitive adhesive has high cohesive strength and superior elasticity, the pressure-sensitive adhesive is likely to be bonded to the surface of various materials under gentle finger pressure and be adhered and removed without residue. Accordingly, the pressure-sensitive adhesive composition must comprise components having high elasticity and adhesion respectively.

Due to the convenience, pressure-sensitive adhesives are widely used in the fabricating process of liquid crystal displays, for example, serving as the adhesive layer of polarizing film.

A polarizing film, also called a polarizer, is utilized to control the polarizing direction of the incident light and allow the polarized light to pass through. Thus the polarizer can be applied in a LCD display panel to increase the contrast value. Referring to FIG. 1, a conventional polarizing film 10 comprises a PVA polarizing base film 12. The method of preparing the PVA polarizing base film 12 comprises dipping a stretched polyvinayl alcohol film in a dichromic dye and baking the obtained film. First and second triacetyl cellulose (TAC) films 14 and 16 are respectively formed on a first and second sides of the PVA polarizing base film 12. To prevent the PVA polarizing base film 12 from scratching, a protective layer 18 is formed on the first triacetyl cellulose (TAC) films 14. A pressure-sensitive adhesive layer 20 is formed on the second triacetyl cellulose (TAC) films 16 and provisionally mounted on a release film 22 before being pasted on a liquid crystal display screen.

The characteristics of pressure-sensitive adhesive for polarizing film comprise the peeling force between adhesive and substrate, the peeling force between adhesive and release film, and adhesive durability. In general, after coating on a substrate, the pressure-sensitive adhesive is subjected to mature treatment at a specific temperature and relative humidity, thereby completing the cross-link reaction of the polymerizable components thereof. The peeling force between the adhesive and the substrate (called adhesive strength) is the most important factor.

The adhesive strength is measured through a method conforming to EIAJ ED-2521A of the Standard of Electric Industrial Association of Japan and indicated by g/25 mm. In general, the peeling force between adhesive of the polarizing film and substrate must be in a range between 100 to 1000 g/25 mm.

The adhesive strength of pressure-sensitive adhesive depends on the degree of crosslinking in the pressure-sensitive adhesive polymerized by a hardener. The polarizing film mounted on the substrate by the pressure-sensitive adhesive is apt to be easily peeled off or curled up when the pressure-sensitive adhesive has a lower degree of crosslinking, resulting in reduced yield and stability of LCD products.

A gel fraction is one index for measuring the degree of crosslinking of the polymerizable components of an adhesive. This index is obtained in such a manner that the adhesive was coated on a substrate and subjected to a mature treatment after several days. The solidified adhesive is scraped off the substrate, collected and weighted as W1. Next, the solidified adhesive is dissolved in ethyl acetate with ultrasonic agitation for 1 hr. The mixture is filtered, and the residual is collected, dried, and weighted as W2. The equation of gel fraction is:

$$\text{Gel fraction} = (W2/W1) \times 100\%$$

The degree of crosslinking of pressure sensitive adhesive used in an LCD can be estimated by gel fraction. The aforementioned method for measuring gel fraction, which is a destructive test, however, has complicated steps and long periods of time (5~6 hr). Therefore, methods for measuring the degree of crosslinking of pressure sensitive adhesive with easy process and high convenience are desirable.

BRIEF SUMMARY OF THE INVENTION

The invention provides a method for measuring the degree of crosslinking in pressure sensitive adhesive, having the advantages of simple steps and short measuring time. The method comprises the following steps: providing a transparent substrate coated with a pressure sensitive adhesive; immersing the transparent substrate in a solvent; measuring the haze of the transparent substrate; and comparing the obtained haze with a predetermined reference, thereby determining the degree of crosslinking of the pressure sensitive adhesive.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The adhesive strength of a pressure sensitive adhesive can be measured by the method for measuring the degree of crosslinking of the invention. In an embodiment of the invention, the method comprises providing a transparent substrate coated with a pressure sensitive adhesive. The transparent substrate can be substrate employed in LCD or transparent optical film, such as a glass substrate, triacetate cellulose film, release film, antireflection film, or polarizing film (i.e, polarizer). Next, the transparent substrate is immersed in a solvent. The solvent can be alcohol, alkane, ether, or ester, such as methanol, ethanol, n-propanol, i-propanol, n-butanol, n-hexane, ethyl ether, tetrahydrofuran, or ethyl acetate. In this step, the surface of the transparent substrate is hazed by the solvent.

After a specific period (such as 2~4 min), the transparent substrate is dried and measured the haze thereof by a haze meter. The haze relates to the amount of directional light (Dr) and the amount of non-directional light (Df), according to the relationship equation:

$$\text{Haze (\%)} = Dr/(Dr+Df) \times 100$$

Figure 1:
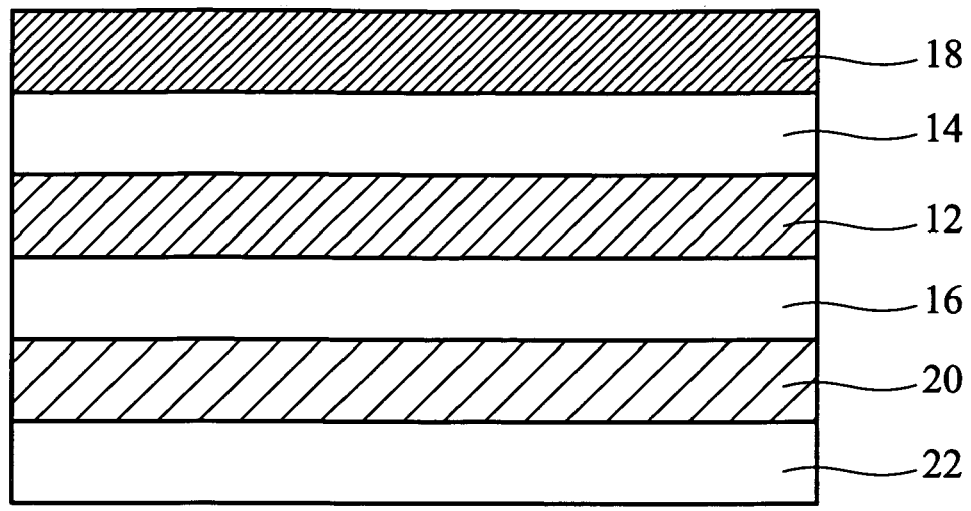
FIG. 1 is a schematic diagram of a conventional polarizing film showing the structure thereof.
Figure 2:
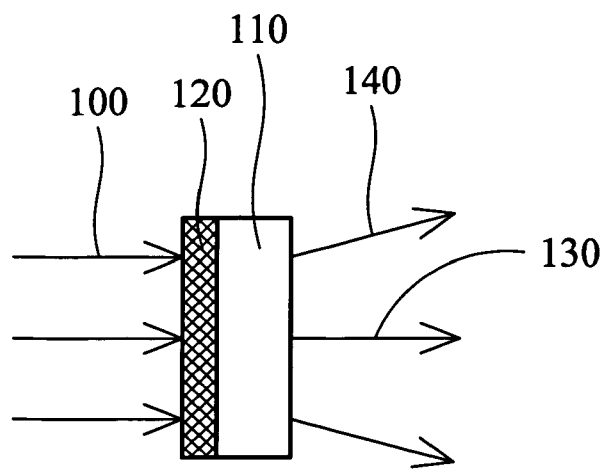
FIG. 2 is a schematic diagram of the method for measuring the haze according to the invention.

Referring to FIG. 2, incident light 100 passes through the transparent substrate 110 from the pressure sensitive adhesive film 120, scattering to form a directional light 130 and non-directional light 140, wherein the angle between the incident light 100 and non-directional light 140 is more than 5°.

The obtained haze is compared with a predetermined reference. Since the haze is negatively related to the degree of crosslinking of a pressure sensitive adhesive, the degree of crosslinking of pressure sensitive adhesive can be concluded. The predetermined reference comprises a database showing the relationship between the haze and the gel fraction of a specific pressure sensitive adhesive. Therefore, the corresponding gel fraction can be obtained by measuring the haze of the pressure sensitive adhesive. For example, the pressure sensitive adhesive has a gel fraction of more than 80% when the haze thereof is less than 40% according to a predetermined reference. A substrate coated with the same kind of the pressure sensitive adhesive has a measured haze of less than 40%, and thus the pressure sensitive adhesive has sufficient degree of crosslinking.

Suitable pressure sensitive adhesives to be measured by the method are not limited and can be natural rubber pressure sensitive adhesive (used in plasters for medical purposes or electrical insulation tape), synthetic rubber pressure sensitive adhesive (styrene butadiene rubber or polyisobutylene rubber), or alkene polymer pressure sensitive adhesive (Poly vinyl phenylene ether or polyacrylate).

Accordingly, the method of the invention enables a surveyor to immediately and conveniently estimate the adhesive strength of a pressure sensitive adhesive.

The following examples are intended to demonstrate this invention more fully without limiting its scope, since numerous modifications and variations will be apparent to those skilled in the art.

Predetermined Reference

EXAMPLE 1

A pressure sensitive adhesive (sold and manufactured under the trade number of TX37 by SOKEN) was coated on polarizer substrates, and cured respectively with hardeners having different weight at 23.2° C. and 50~70% RH. Next, the gel fractions were measured by conventional method. The results were shown in Table 1:

TABLE 1

| hardener(g) | Gel Fraction % | | | |
|---|---|---|---|---|
| | 4th day | 5th day | 6th day | 7th day |
| 0.055 | 69.45% | 78.29% | 85.51% | 85.57% |
| 0.04 | 63.46% | 72.74% | 76.52% | 78.58% |
| 0.03 | 55.42% | 67.81% | 71.80% | 71.47% |
| 0.025 | 42.00% | 58.08% | 66.54% | 70.83% |

Next, the polarizer substrates coated with the pressure sensitive adhesive were cured respectively with hardeners having different weight at 23.2° C. The polarizer substrates were immersed in ethyl acetate for 2 min. After drying, the hazes of the polarizer substrates were measured by the method of the invention. The results were shown in Table 2:

TABLE 2

| hardener(g) | Haze % | | | |
|---|---|---|---|---|
| | 4th day | 5th day | 6th day | 7th day |
| 0.055 | 51.64% | 46.98% | 42.31% | 41.59% |
| 0.04 | 73.23% | 62.86% | 55.49% | 51.42% |
| 0.03 | 87.34% | 79.29% | 70.09% | 65.49% |
| 0.025 | 91.23% | 88.32% | 83.27% | 81.09% |

Figure 3:
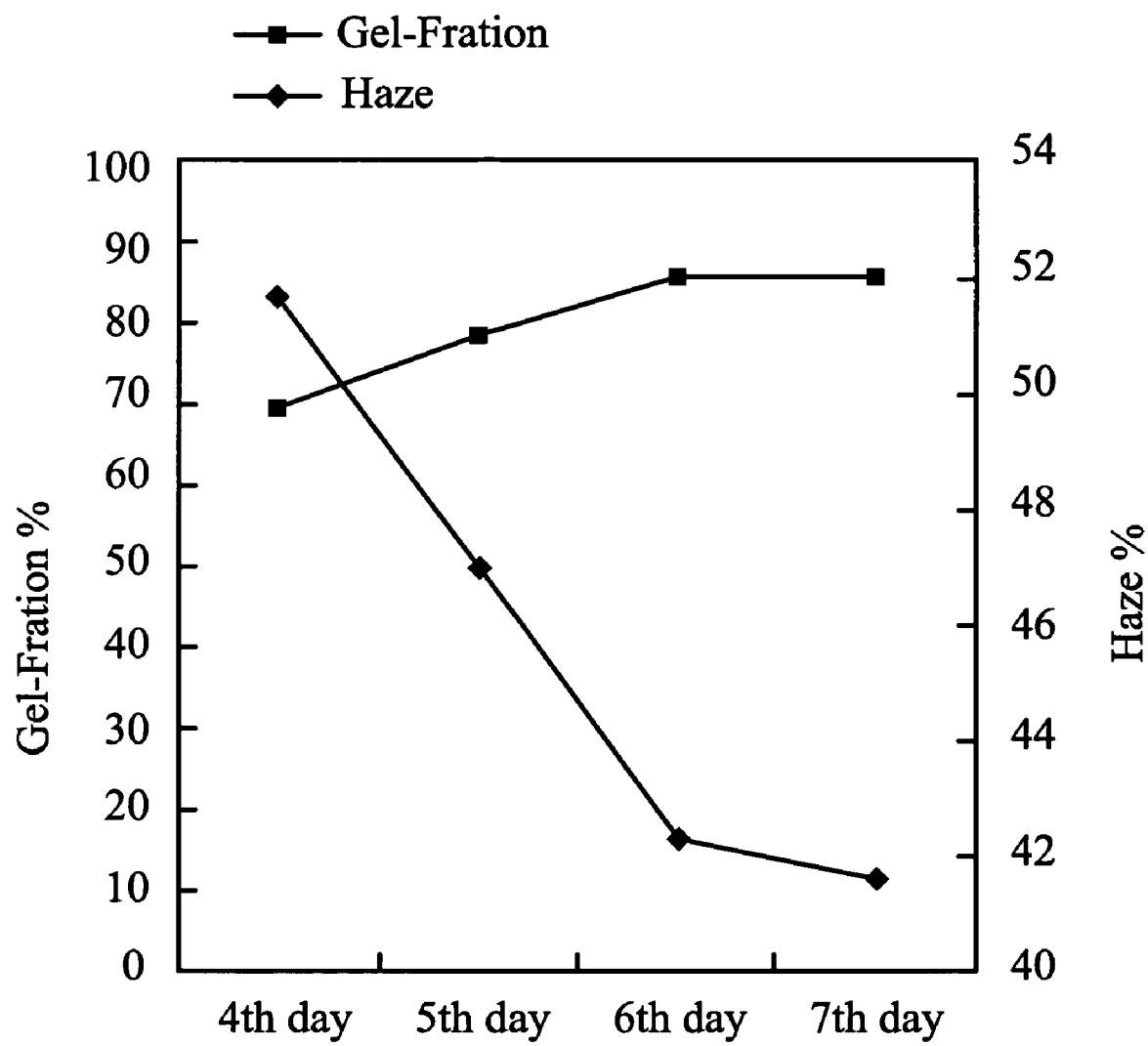
FIGS. 3 and 4 are graphs plotting haze against gel fraction of the pressure sensitive adhesives as disclosed in Example 1.
Figure 4:
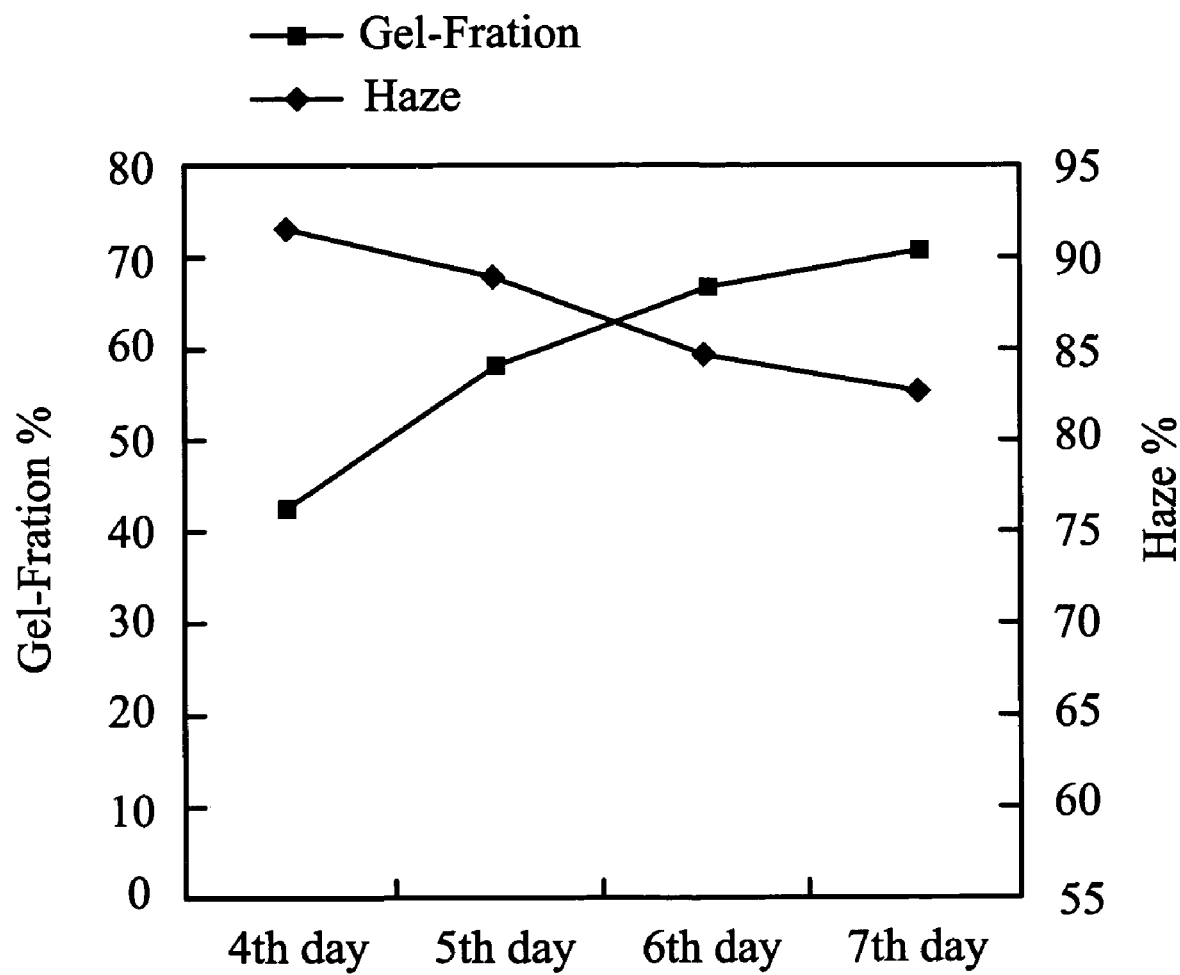

FIGS. 3 and 4 respectively show the relationship between haze and gel fraction with the hardener in an amount of 0.055 g and 0.025 g. Accordingly, the measured haze was negatively related to the gel fraction. A surveyor can expect the approximate gel fraction of a sample when obtaining the haze measured by the method of the invention.

Repeatability Test

EXAMPLE 2

A pressure sensitive adhesive (sold and manufactured under the trade number of TX37 by SOKEN) with 0.03 g hardener was coated on four polarizer substrates respectively and cured at 23.2° C. and 50~70% RH. Further, a pressure sensitive adhesive (sold and manufactured under the trade number of TX37 by SOKEN) with 0.04 g hardener was coated on other four polarizer substrates respectively and cured at 23.2° C. and 50~70% RH. The polarizer substrates were immersed in ethyl acetate for 2 min. After drying, the hazes of the polarizer substrates were measured by the method of the invention. The results were shown in Table 3.

TABLE 3

| hardener(g) | Sample 1 | Sample 1 | Sample 3 | Sample 4 |
|---|---|---|---|---|
| | Gel Fraction % | | | |
| 0.04 | 75.85% | 76.04% | 76.5% | 76.58% |
| 0.03 | 69.42% | 70.81% | 71.80% | 70.47% |
| | Haze % | | | |
| 0.04 | 50.19% | 50.38% | 50.28% | 50.42% |
| 0.03 | 64.54% | 64.3% | 64.77% | 65.49% |

As shown in Table 3, since the difference of haze is less than 1%, the method of the invention has high repeatability.

EXAMPLE 3

Pressure sensitive adhesives (sold and manufactured under the trade number of TX37 by SOKEN) with 0.03 g and 0.04 g hardener were respectively coated on polarizer substrates and cured at 23.2° C. and 50~70% RH. The polarizer substrates were immersed in ethanol for 2 min. After drying, the hazes of the polarizer substrates were measured by the method of the invention. The results were shown in Table 4.

TABLE 4

| | Hardener(g) | | | |
|---|---|---|---|---|
| | 0.055 | 0.04 | 0.03 | 0.025 |
| Haze % | 11.0 | 13.5 | 18.1 | 21.5 |
| Gel Fraction % | 84.2 | 77.4 | 68.1 | 60.2 |

Figure 5:
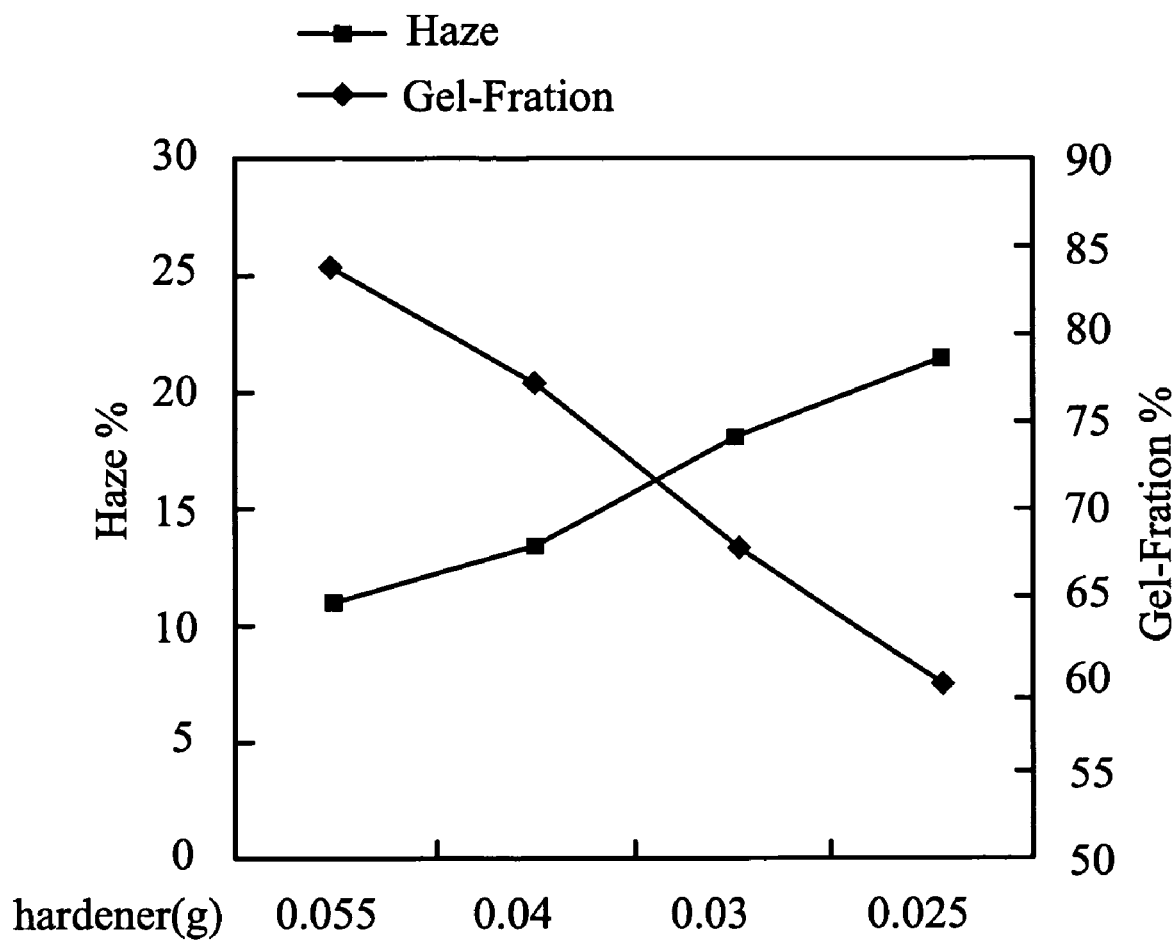
FIG. 5 is a graph plotting haze against gel fraction of the pressure sensitive adhesive as disclosed in Example 3.

FIG. 5 shows the relationship between haze and gel fraction of Example 3. Accordingly, the haze is negatively related to the degree of crosslinking of a pressure sensitive adhesive.

EXAMPLE 4

Pressure sensitive adhesive (sold and manufactured under the trade number of TX37 by SOKEN) was coated on polarizer substrates and cured at 23.2° C. and 50~70% RH. The PVA substrates were immersed in ethyl acetate for 2 min, 3 min and 4 min respectively. After drying, the hazes of the polarizer substrates were measured by the method of the invention. The results were shown in Table 5.

TABLE 5

| | Haze % | | |
|---|---|---|---|
| | 2 min | 3 min | 4 min |
| Sample 1 | 50.19 | 41.23 | 33.27 |
| Sample2 | 50.38 | 41.02 | 33.82 |

Accordingly, the obtained haze is reduced with extending immersion time. Therefore, a surveyor can adjust the immersion time optionally. In an exemplary embodiment, the immersion time can be 2~4 min.

Accordingly, the method for measuring the degree of crosslinking of pressure sensitive adhesive of the invention has the advantages of simple steps and short measuring time (less than 10 min), and is thereby suitable for use in on-line reliability test. Further, the method is also suitable for sifting out the best mature conditions of pressure sensitive adhesives.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for measuring the degree of crosslinking of pressure sensitive adhesive, comprising:
    providing a transparent substrate coated with a pressure sensitive adhesive;
    immersing the transparent substrate in a solvent;
    measuring the haze of the transparent substrate; and
    comparing the obtained haze with a predetermined reference, thereby concluding the degree of crosslinking of the pressure sensitive adhesive.

2. The method as claimed in claim 1, wherein the transparent substrate comprises substrate employed in LCD or transparent optical film.

3. The method as claimed in claim 1, wherein the transparent substrate is glass.

4. The method as claimed in claim 1, wherein the transparent substrate comprises triacetate cellulose film, release film, antireflection film, or polarizing film.

5. The method as claimed in claim 1, wherein the pressure sensitive adhesive comprises natural rubber pressure sensitive adhesive, synthetic rubber pressure sensitive adhesive, or alkene polymer pressure sensitive adhesive.

6. The method as claimed in claim 1, wherein the pressure sensitive adhesive is polyacrylate.

7. The method as claimed in claim 1, wherein the transparent substrate is immersed in the solvent for 2~4 min.

8. The method as claimed in claim 1, wherein the solvent comprises alcohol, alkane, ether, or ester.

9. The method as claimed in claim 1, wherein the solvent comprises methanol, ethanol, n-propanol, i-propanol, n-butanol, n-hexane, ethyl ether, tetrahydrofuran, or ethyl acetate.

10. The method as claimed in claim 1, wherein the predetermined reference indicates the relationship between haze and gel fraction.

* * * * *